US012653846B2

(12) United States Patent
Heide

(10) Patent No.: US 12,653,846 B2
(45) Date of Patent: Jun. 16, 2026

(54) MICROBIOME COMPOSITIONS

(71) Applicant: B.Y.M. TECHNOLOGIES, London (GB)

(72) Inventor: Chiara Heide, London (GB)

(73) Assignee: B.Y.M. TECHNOLOGIES, London (GB)

( * ) Notice: Subject to any disclaimer, the term of this patent is extended or adjusted under 35 U.S.C. 154(b) by 335 days.

(21) Appl. No.: 18/273,839

(22) PCT Filed: Jan. 25, 2022

(86) PCT No.: PCT/EP2022/051637
§ 371 (c)(1),
(2) Date: Jul. 24, 2023

(87) PCT Pub. No.: WO2022/157390
PCT Pub. Date: Jul. 28, 2022

(65) Prior Publication Data
US 2024/0390430 A1 Nov. 28, 2024

(30) Foreign Application Priority Data

Jan. 25, 2021 (GB) ..................................... 2100945

(51) Int. Cl.
| | |
|---|---|
| *A61K 35/741* | (2015.01) |
| *A61K 9/00* | (2006.01) |
| *A61K 35/00* | (2006.01) |
| *A61K 47/26* | (2006.01) |
| *A61K 47/34* | (2017.01) |
| *A61K 47/36* | (2006.01) |
| *A61P 31/04* | (2006.01) |

(52) U.S. Cl.
CPC .......... *A61K 35/741* (2013.01); *A61K 9/0034* (2013.01); *A61K 47/26* (2013.01); *A61K 47/34* (2013.01); *A61K 47/36* (2013.01); *A61P 31/04* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 2006/0257374 A1 | 11/2006 | Williams et al. | |
| 2012/0276054 A1 | 11/2012 | Williams et al. | |
| 2015/0147375 A1 | 5/2015 | Jaeger | |
| 2019/0343898 A1* | 11/2019 | Sinkkonen | A61K 8/99 |

FOREIGN PATENT DOCUMENTS

| | | | | |
|---|---|---|---|---|
| AU | 4061702 A * | 4/2003 | .......... | A61K 9/2826 |
| FR | 2302103 A1 | 9/1976 | | |
| WO | 9619119 A1 | 6/1996 | | |
| WO | 03082306 A1 | 10/2003 | | |
| WO | WO-2018053140 A1 * | 3/2018 | ............. | A61P 27/16 |
| WO | 2020084589 A1 | 4/2020 | | |

OTHER PUBLICATIONS

Fenster et al. Microorganisms Jul. 2019, 83; doi: 10.3390/microorganisms7030083 (17 pages).*
Karunker et al. (2013) PLoS One 8(4): e61850. doi:10.1371/journal.pone.0061850.*
International Search Report mailed May 13, 2022 in Application PCT/EP2022/051637.
European Search Report mailed Aug. 24, 2021 in Application GB2100945. I.
Ghosh, Chandradhish, et al. "Alternatives to conventional antibiotics in the era of antimicrobial resistance." Trends in microbiology 27.4 (2019): 323-338.
Bonfiglio, Giulia, et al. "Insight into the Possible Use of the Predator Bdellovibrio Bacteriovorus as a Probiotic." Nutrients, vol. 12, No. 8, Jul. 2020.
Basavaprabhu, H. N., K. S. Sonu, and R. Prabha. "Mechanistic insights into the action of probiotics against bacterial vaginosis and its medlated preterm birth: An overview." Microbial pathogenesis 141 (2020).

* cited by examiner

*Primary Examiner* — Oluwatosin A Ogunbiyi
(74) *Attorney, Agent, or Firm* — NIXON PEABODY LLP; David S. Resnick; Nicole D. Kling

(57) ABSTRACT

According to the invention there is provided an antimicrobial agent for use in maintaining or re-establishing a healthy genital microbiome, wherein the antimicrobial agent is a predatory bacterium.

6 Claims, 7 Drawing Sheets

<u>Figure 1</u>

Figure 7
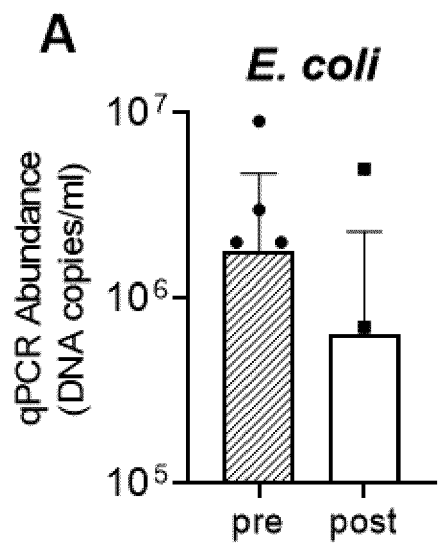
A *E. coli*
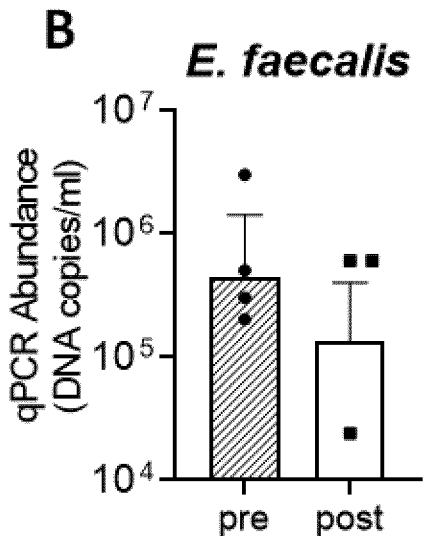
B *E. faecalis*
C *Lactobacillus* spp.
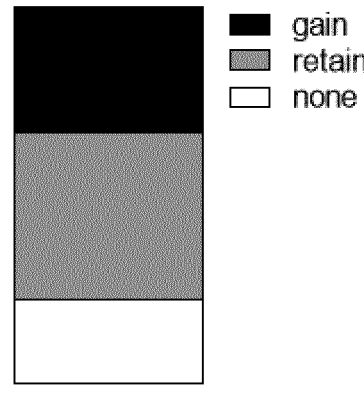
■ gain
▨ retain
□ none
Total=9

MICROBIOME COMPOSITIONS

CROSS-REFERENCE TO RELATED APPLICATIONS

This application is a 35 U.S.C. § 371 National Phase Entry Application of International Application No. PCT/EP2022/051637 filed Jan. 25, 2022, which claims benefit under 35 U.S.C. § 119(a) of GB Application No. 2100945.1 filed Jan. 25, 2021, the contents of which are incorporated herein by reference in their entireties.

FIELD OF INVENTION

The present invention relates to a predatory bacterium and its use as an antimicrobial agent. The invention relates to the predatory bacterium for use in maintaining or restoring a healthy genital microbiome. The use can also include preventing or treating gram-negative bacterial infections. The invention also relates to a method of manufacturing a composition comprising a predatory bacterium for uses according to the invention.

BACKGROUND OF THE INVENTION

A healthy vaginal flora is dominated by various gram-positive *Lactobacillus* species. Lactobacilli help to keep the vagina healthy by producing lactic acid, hydrogen peroxide, and other substances that inhibit the colonization and growth of harmful microorganisms (yeast and bacteria) in the female urogenital area. This natural protective function of the gram-positive *Lactobacillus* species is also referred to as colonization resistance and acts as a protective barrier and immune defence against foreign infections. Changes in pH, hormone levels, antibiotic intake, and sexual intercourse can all lead to the killing of lactobacilli resulting in a reduced protection from external microorganisms and infections.

Gram-negative bacteria such as *Escherichia coli*, *Pseudomonas* strains and *Klebsiella* strains are responsible for a large range of bacterial infections in the genital and specifically vaginal area, and are one of the main causes for recurrent urinary tract infections. These bacteria often originate from the rectum of women, and transfer via the perineum to colonize the vaginal area causing recurring infections. This is particularly evident when the vaginal flora is unbalanced, as this weakens the native protective layer in the vaginal area. These bacteria may also originate from external influences, including via the interaction with the male genital microbiome via sexual intercourse.

On top of the economic and societal burden, genital bacterial infections including UTIs are becoming increasingly difficult to treat due to the rise in antibiotic resistant bacteria. Often a series of broad-spectrum antibiotics are used to kill harmful bacteria. As these are not specific or localised, the antibiotics also kill beneficial bacteria in the gut and genital flora. Overuse of antibiotics is also a significant problem, similarly leading to destruction of beneficial gut and genital flora, causing a variety of negative side effects.

There is therefore a need for novel solutions to address these problems in a more targeted and sustainable fashion.

SUMMARY

Provided herein is an antimicrobial agent for use in maintaining or re-establishing a healthy genital microbiome, wherein the antimicrobial agent is a predatory bacterium.

Also provided herein is an antimicrobial agent for use in preventing or treating a genital bacterial infection, wherein the antimicrobial agent is a predatory bacterium.

Also provided herein is a formulation comprising:
a. a composition comprising an antimicrobial agent and one or more excipients; and
b. one or more silicon-based polymers.

Also provided herein is a method of maintaining or re-establishing a subject's healthy genital microbiome comprising administering a predatory bacterium to the external genital area of a subject and/or the vagina of a subject.

Also provided herein is a method of prophylaxis or treatment of a gram-negative bacterial infection in a subject in need thereof comprising administering a predatory bacterium to the external genital area of a subject and/or the vagina of a subject.

Finally, provided herein is a method of manufacturing a composition comprising *Bdellovibrio bacteriovorus* (Bdello) as an antimicrobial agent, wherein the Bdello is:
a. cultured;
b. isolated;
C. combined with one or more excipients; and
d. freeze-dried or spray-dried.

BRIEF DESCRIPTION OF THE FIGURES

FIG. 7. (A) Absolute abundance of *E. coli* was reduced post-application of *B. bacteriovorus*, with 50% (2/4) of those originally colonised having none detected. (B) *E. faecalis* was also reduced post-application, with one participant losing it entirely. (C) 33.33% (3/9) of participants gained *Lactobacillus* spp. following 7 days application of *B. bacteriovorus*, with another 44.44% (4/9) retaining the lactobacilli that they were colonized with pre-application.

DETAILED DESCRIPTION

1. Definitions

Figure 1:
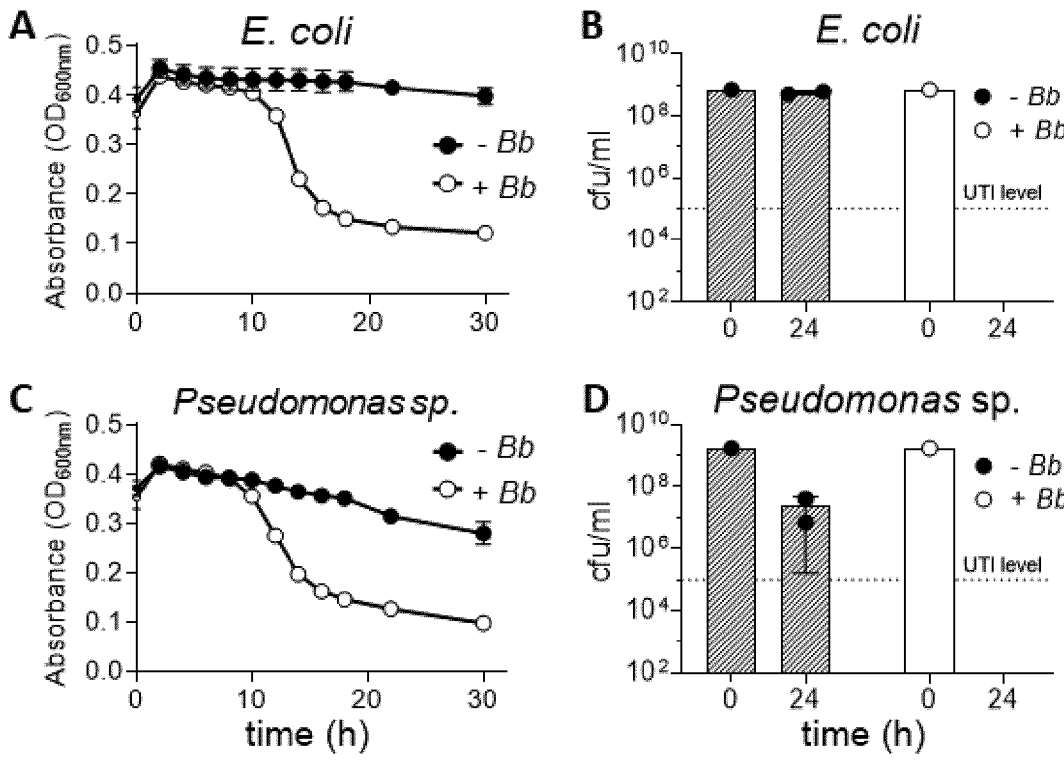
FIG. 1. *B. bacteriovorus* kills *E. coli* (A, B) and *Pseudomonas* sp. (C, D). Optical density was measured over 30 h (A, C) with a reduction seen in the predator-treated samples. Killing was measured concurrently by counting colony forming units (CFU) at 0 and 24 h after incubation with *B. bacteriovorus*. Both *E. coli* (B) and *Pseudomonas* sp. (D), in the presence of *B. bacteriovorus*, were undetectable at T24. Limit of detection=100 cfu/ml
Clinical UTI level: ≥$10^5$ cfu/ml (dotted line)
Bb: *B. bacteriovorus*

Unless otherwise defined herein, scientific and technical terms shall have the meanings that are commonly understood by those of ordinary skill in the art. Further, unless otherwise required by context, singular terms shall include pluralities and plural terms shall include the singular.

The singular terms "a," "an," and "the" include plural referents unless context clearly indicates otherwise. Similarly, the word "or" is intended to include "and" unless the context clearly indicates otherwise.

In the specification and claims, the term "about" is used to modify, for example, the proportion of a particular bacterial species in a particular microbiome. The term "about" refers to variation in the numerical quantity that can occur, for example, through typical measuring procedures for microbial populations or through inadvertent error in these procedures. Where modified by the term "about" the claims appended hereto include equivalents to these quantities.

As used herein, "administer" or "administration" refers to the act of topically applying or otherwise physically delivering a substance as it exists outside the body (e.g., Bdello) to a patient, such as by ingestion or any other method of physical delivery described herein or known in the art. When an infection, or a symptom thereof, is being treated, administration of the substance typically occurs after and/or with the onset of the infection or symptoms thereof. When a disease, or symptoms thereof, are being prevented, administration of the substance typically occurs before the onset of the disease or symptoms thereof.

As used herein, the term "composition" is intended to encompass a product containing the specified ingredients (e.g. Bdello, and an excipient) in, optionally, the specified amounts, as well as any product which results, directly or indirectly, from combination of the specified ingredients in, optionally, the specified amounts.

As used herein the term "comprising" or "comprises" is used with reference to uses, compositions, methods, and respective component(s) thereof, that are essential to the method or composition, yet open to the inclusion of unspecified elements, whether essential or not.

The term "consisting of" refers to uses, compositions, methods, and respective components thereof as described herein, which are exclusive of any element not recited in that description of the example.

As used herein the term "consisting essentially of" refers to those elements required for a given example. The term permits the presence of elements that do not materially affect the basic and novel or functional characteristic(s) of that example.

An "effective amount" refers to an amount effective, at dosages and for periods of time necessary, to achieve the desired effect, including a therapeutic or prophylactic (i.e. preventative) result. A "therapeutically effective amount" refers to the minimum concentration required to effect a measurable improvement or prevention of a particular disorder. A therapeutically effective amount herein may vary according to factors such as the disease state, age, sex, and weight of the patient, and the ability of Bdello to elicit a desired response in the individual. A therapeutically effective amount is also one in which toxic or detrimental effects of the Bdello are outweighed by the therapeutically beneficial effects. A "prophylactically effective amount" refers to an amount effective, at the dosages and for periods of time necessary, to achieve the desired prophylactic result. In some examples, "effective amount" as used herein also refers to the amount of Bdello to achieve a specified result (e.g. inhibition of a bacterial infection).

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

As used herein, the terms "prevent", "preventing", and "prevention" refer to prophylaxis of a bacterial infection, resulting from the administration of a composition according to the invention.

The terms "treat", "treatment" and "treating" refer to the reduction or amelioration of the progression, severity, and/or duration of a bacterial infection.

The term "probiotic" as used herein refers to a composition comprising live microorganisms.

Other terms are defined herein within the description of the various examples of the disclosure.

2. Predatory Bacteria and Uses

Predatory bacteria are naturally occurring bacteria that selectively target and kill certain gram-negative bacteria. This 'predator-prey' relationship is similar to those found in the higher tropic levels of the ecosystem, involving larger hunting animals feeding upon prey. In the case of microorganisms, predatory bacteria are capable of destroying 'prey' gram-negative bacterium via periplasmic or endobiotic mechanisms. Periplasmic mechanisms involve the predator bacteria invading a prey cell, and proliferating within its periplasm. Endobiotic mechanisms involve the predator bacteria attaching to a prey cell and consuming it from the outside. Prey is then lysed, after which the process is continuously repeated.

The present invention utilises predatory bacteria as an antimicrobial agent to balance the natural microbiome of the genital area, particularly the vagina, by reducing harmful bacteria, whilst allowing beneficial bacteria to replenish in the genital flora. In this way, the predatory bacteria have a dual function and may be considered "amphibiotic", compared to e.g. antibiotic approaches that unselectively reduce all bacteria (both harmful and beneficial) but do not replenish beneficial bacteria, and probiotic approaches that aim to boost numbers of beneficial bacteria but do not target harmful bacteria.

In the present invention, the antimicrobial agent is a predatory bacterium. In some embodiments, the antimicrobial agent belongs to the proteobacteria. In some embodiments, the antimicrobial agent is a *Bdellovibrionaceae* species (referred to herein as Bdello). In some embodiments, the antimicrobial agent is a *Bdellovibrio* species. In some embodiments, the antimicrobial agent is a *Bdellovibrio bacteriovorus*. In some embodiments, the antimicrobial agent is a *Bdellovibrio bacteriovorus* HD100 strain. In some embodiments, the antimicrobial agent is a *Bdellovibrio bacteriovorus* 109J strain. In some embodiments, the antimicrobial agent is a *Bdellovibrio bacteriovorus* 118 strain. Bdello is part of the Proteobacteria phylum, of the class Oligoflexia.

In some embodiments, the antimicrobial agent is a naturally occurring species i.e. it is not genetically engineered. In some embodiments, the antimicrobial agent is genetically engineered or genetically modified.

Bdello is a ubiquitous gram-negative bacteria, found in soil, rivers, lakes, seawater, marine sediments and sewage. It can also be isolated from human and animal. Thus, in some embodiments, the Bdello is isolated from one or more of soil, rivers, lakes, seawater, marine sediments and sewage. In some embodiments, the Bdello is isolated from a human and/or animal.

In some embodiments, the antimicrobial agent inhibits the growth of pathogenic bacteria. In some embodiments, the antimicrobial agent inhibits the growth of pathogenic, non-commensal bacteria. Commensal bacteria are bacteria that are part of the normal flora in a host and may provide a protective response to pathogenic bacteria. Pathogenic bacteria may be gram-negative (for example *E. coli*), gram-positive (for example, *E. faecalis* and *U. parvum*) or gram-variable (for example, *G. vaginalis* and *M. curtisii*).

In some embodiments, the antimicrobial agent inhibits the growth of gram-negative bacteria, including but not limited to species of one or more of the following genera: *Escherichia, Klebsiella, Gardnerella, Prevotella, Bacteroides, Mobiluncus, Salmonella, Proteus, Pseudomonas, Chlamydia,* and *Neisseria*. In some embodiments, the gram-negative bacteria is *E. coli*. In some embodiments, the gram-negative bacteria is *E. cloacae*. In some embodiments, the gram-negative bacteria is *P. aeruginosa*. In some embodiments, the gram-negative bacteria is *K. pneumoniae*. In some embodiments, the gram-negative bacteria is *P. mirabilis*. In some embodiments, the gram-negative bacteria is *N. gonorrhoede*. In some embodiments, the gram-negative bacteria is *E. coli* and *P. aeruginosa*. In some embodiments, the gram-negative bacteria is *E. coli* and *K. pneumoniae*. In some embodiments, the gram-negative bacteria is *E. coli* and *P. mirabilis*. In some embodiments, the gram-negative bacteria is *E. coli* and *N. gonorrhoeae*. In some embodiments, the gram-negative bacteria is *E. coli, P. aeruginosa, K.*

*pneumoniae* and/or *P. mirabilis*. In some embodiments, the gram-negative bacteria is any combination of bacteria listed above.

In some embodiments, the antimicrobial agent inhibits the growth of non-commensal gram-positive bacteria, particularly biofilm-forming non-commensal gram-positive bacteria. In some embodiments, the gram-positive bacteria is *E. faecalis*. In some embodiments, the gram-positive bacteria is *U. parvum*. In some embodiments the gram-positive bacteria has an altered or missing cell wall.

In some embodiments, the antimicrobial agent does not inhibit the growth of gram-positive bacteria, and in particular commensal gram-positive bacteria. In some embodiments, said gram-positive bacteria is a *Lactobacillus* species. In some embodiments, said gram-positive bacteria is a *Bifidobacterium* species. In some embodiments, the gram-positive bacteria comprise *Lactobacillus* and *Bifidobacterium* species.

In this way, the present invention is able to re-build or maintain the natural protective barrier of the genital flora to promote a healthy urinary tract and boost intimate health, without the need for e.g. antibiotics (prophylactic or otherwise).

Provided herein is use of the antimicrobial agent as described anywhere herein as a probiotic for maintaining a healthy genital microbiome. In some embodiments, the genital microbiome is a vaginal microbiome.

Thus, also provided herein is use of the antimicrobial agent as described anywhere herein as a probiotic for maintaining a healthy vaginal microbiome. A healthy vaginal microbiome is dominated by *Lactobacillus* species. The *Lactobacillus* species can include *L. crispatus, L. iners, L. jenseniil* and/or *L. gasseri*, and preferably *L. acidophilus*.

In some embodiments, the vaginal microbiome comprises a mixed population of gram-positive bacteria such as *Lactobacillus* and *Bifidobacterium* that protect the vaginal area from infections, such as UTIs caused by *E. coli, P. aeruginosa, P. mirabilis* and/or *K. pneumoniae*.

A healthy vaginal microbiome is dominated by *Lactobacillus* species. In some embodiments, a healthy vaginal microbiome comprises at least 50% *Lactobacillus* species. In some embodiments, a healthy vaginal microbiome comprises at least 70% *Lactobacillus* species. In some embodiments, a healthy vaginal microbiome also comprises *Bifidobacterium* species, e.g. at least 2% *Bifidobacterium* species. In an embodiment, a healthy vaginal microbiome comprises about 70% to 95% *Lactobacillus* species and about 5% to 30% *Bifidobacterium* species. In an embodiment, a healthy vaginal microbiome comprises about 90% *Lactobacillus* species and about 10% *Bifidobacterium* species. This gram-positive dominated composition is unlike other microbiomes, such as the gut microbiome where a mixed population of gram-positive and gram-negative bacteria is representative of a healthy gut flora.

In some embodiments, the *Lactobacillus* species include *L. iners, L. crispatus, L. gasseri, L. jensenii* and/or *L. acidophilus*. In some embodiments, the *Bifidobacterium* species include *B. bifidum, B. breve, B. adolescentis* and/or *B. longum*.

In some embodiments, the antimicrobial agent maintains a healthy genital microbiome, particularly a healthy vaginal microbiome, by restoring the natural balance or ratio of gram-negative and gram-positive bacteria in the genital area. In some embodiments, the antimicrobial agent substantially restores the vagina flora to at least 50% *Lactobacillus* species. In some embodiments, the antimicrobial agent substantially restores the vagina flora to at least 70% *Lac-*

*tobacillus* species. In some embodiments, the antimicrobial agent substantially restores the vagina flora to also comprise at least 2% *Bifidobacterium* species. In an embodiment, the antimicrobial agent substantially restores the vagina flora to about 70 to 95% *Lactobacillus* species and about 30 to 5% *Bifidobacterium* species. In an embodiment, the antimicrobial agent substantially restores the vagina flora to about 90% *Lactobacillus* species and about 10% *Bifidobacterium* species. In some embodiments, an imbalance of gram-negative and gram-positive bacteria in the vagina is caused by a bacterial infection e.g. a gram-negative bacterial infection, or treatment with antibiotics.

In some embodiments, the antimicrobial agent promotes the growth of a *Lactobacillus* species relative to gram-negative bacterial species. In some embodiments, the antimicrobial agent promotes the growth of a *Lactobacillus* species relative to *E. coli*, thus reducing the urogenital pH. Promoting the growth of beneficial bacteria (e.g. Lactobacilli) may effectively inhibit the growth of pathogenic bacteria (e.g. *E. coli*) associated with urogenital infections and help maintain a healthy microflora balance in the urogenital area.

The vaginal microbiome is the living microorganism population in the vagina. The urogenital area refers to the vulva, vagina, urinary tract, bladder and surrounding areas.

In some embodiments, the antimicrobial agents are for use in a human. In some embodiments, the antimicrobial agents are for use in adult women. In some embodiments, the antimicrobial agents are for use in adult men. In some embodiments, the antimicrobial agents are for use in post-menopausal women. In some embodiments, the antimicrobial agents for use in infants.

Provided herein is a method of maintaining a healthy genital microbiome in a subject comprising administering a composition comprising Bdello, and one or more excipients to a subject, by topically applying the composition to the subject's external genital area. In some embodiments, the subject is female, and the method comprises topically applying the composition to the female subject's external genital area and/or vagina. In some embodiments, the subject is male. In some embodiments, the external genital area comprises the rectum, perineum and/or vulva (where applicable).

In some embodiments, the antimicrobial agent is not for medical use.

Thus, provided herein is a non-therapeutic method of maintaining or re-establishing a healthy genital microbiome, comprising the steps of applying an antimicrobial agent as described anywhere here to a subject's external genital area. In some embodiments, the genital microbiome is a vaginal microbiome.

Also provided herein is a non-therapeutic use of a composition comprising the antimicrobial agent as described anywhere herein, for maintaining or re-establishing a healthy genital microbiome. In some embodiments, the genital microbiome is a vaginal microbiome.

Antibacterial Use

Provided herein is an antimicrobial agent as described anywhere herein for use in treating or inhibiting a genital bacterial infection. In some embodiments, the antimicrobial agent is *Bdellovibrio bacteriovorus*. In some embodiments, the antimicrobial agent is *Bdellovibrio bacteriovorus* HD100 strain. In some embodiments, the infection is a vaginal bacterial infection.

Also provided herein is an antimicrobial agent as described anywhere herein for use in preventing a urinary tract infection. In some embodiments, the antimicrobial agent is for topical administration to the external genital area. In some embodiments, the antimicrobial agent is for topical administration to the external female genital area. In some embodiments, the antimicrobial agent is Bdello, wherein the Bdello is for topical administration to the external genital area. In some embodiments, the antimicrobial agent is Bdello, wherein the Bdello is for topical administration to the external female genital area. In some embodiments, the antimicrobial agent e.g. Bdello is for topical administration to the external genital area and/or vagina.

Also provided herein is an antimicrobial agent as described anywhere herein for use in preventing a genital bacterial infection. In some embodiments, the bacterial infection is a vaginal bacterial infection. In this case, administration of the antimicrobial agent to the external genital area and/or vagina stops transfer of the pathogenic bacteria from the rectum to the vagina, thus preventing a bacterial infection.

In some embodiments, the infection is bacterial vaginosis. In some embodiments, the infection is aerobic vaginitis. In some embodiments, the infection is a pathogenic bacterial infection. In some embodiments, the infection is a pathogenic, non-commensal bacterial infection. Said pathogenic, non-commensal bacterial infection may be caused by gram-negative bacteria (for example *E. coli*), gram-positive bacteria (for example, *E. faecalis* and *U. parvum*) or gram-variable bacteria (for example, *G. vaginalis* and *M. curtisii*). In some embodiments, the infection is a gram-negative bacterial infection.

In some embodiments, the infection is caused by a species of one or more of the following genera: *Escherichia, Klebsiella, Gardnerella, Prevotella, Bacteroides, Mobiluncus, Salmonella, Proteus, Pseudomonas, Chlamydia* and *Neisseria*. In some embodiments, the infection is caused by *E. coli*. In some embodiments, the infection is caused by *E. cloacae*. In some embodiments, the infection is caused by *P. aeruginosa*. In some embodiments, the infection is caused by *K. pneumoniae*. In some embodiments, the infection is caused by *P. mirabilis*. In some embodiments, the gram-negative bacteria is *N. gonorrhoeae*. In some embodiments, the infection is caused by *E. coli* and *P. aeruginosa*. In some embodiments, the infection is caused by *E. coli* and *K. pneumoniae*. In some embodiments, the infection is caused by *E. coli* and *P. mirabilis*. In some embodiments, the gram-negative bacteria is *E. coli* and *N. gonorrhoeae*. In some embodiments, the infection is caused by *E. coli, P. aeruginosa, K. pneumoniae* and/or *P. mirabilis*. In some embodiments, the infection is caused by any combination of the above listed bacteria.

In some embodiments, the infection is caused by non-commensal gram-positive bacteria, particularly biofilm-forming non-commensal gram-positive bacteria. In some embodiments, the gram-positive bacteria is *E. faecalis*. In some embodiments, the gram-positive bacteria is *U. parvum*.

In some embodiments, the antimicrobial agent inhibits biofilm formation. In some embodiments, the antimicrobial agent degrades biofilm.

In some embodiments, the antimicrobial agent is for administration without a bacteriophage.

In some embodiments, the antimicrobial agent inhibits growth of gram-negative bacteria causing a bacterial infection and does not inhibit growth of gram-positive bacteria.

In some embodiments, the infection is a sexually transmitted infection, such as gonorrhoea and/or chlamydia.

In some embodiments, the infection is caused by the transfer of harmful bacterial species as described anywhere herein from one subject to another (and vice versa) via sexual intercourse. In some embodiments, the harmful bacteria are transferred from the genital area of one subject to another.

Provided herein is an antimicrobial agent as described anywhere herein for use in inhibiting growth of gram-negative bacteria in the genital area. In some embodiments, the antimicrobial agent is Bdello. In some embodiments, the genital area comprises a vagina. Similarly, provided herein is a method of inhibiting growth of gram-negative bacteria in the genital area, the method comprising administering an antimicrobial agent as described anywhere herein to a patient. In some embodiments, the antimicrobial agent is Bdello. In some embodiments, the genital area comprises a vagina.

In some embodiments, the antimicrobial agent is for use in altering the ratio of gram-negative bacteria and gram-positive bacteria in the genital area by killing or inhibiting growth of gram-negative bacteria and not inhibiting growth of gram-positive bacteria. Thus, in some embodiments, the antimicrobial agent is for use in restoring the genital flora of a patient. In some embodiments, the antimicrobial agent is for use in restoring the natural microbiome of the genital area thereby preventing or reducing bacterial infections in the genital area. Methods of the same are also encompassed by the invention.

In some embodiments, the antimicrobial agent is for medical use. In some embodiments, the antimicrobial agent is for use in the prophylaxis and/or treatment of a genital bacterial infection in a human subject in need thereof. In some embodiments, the antimicrobial agent is for use in the prophylaxis and/or treatment of a urinary tract infection (UTI) in a human subject in need thereof. In some embodiments, the antimicrobial agent is for use in the prophylaxis and/or treatment of a UTI caused by E. coli.

Prophylaxis means prevention of a bacterial infection, which is achieved herein by administration of a composition of the invention to a subject.

Provided herein is a method of treating a genital gram-negative bacterial infection, comprising administering a composition comprising the antimicrobial agent as described anywhere herein to the external genital area of a patient in need thereof. In some embodiments, the genital gram-negative bacterial infection is a vaginal gram-negative bacterial infection.

Provided herein is a method of treating a gram-negative urinary tract bacterial infection, comprising administering a composition comprising the antimicrobial agent as described anywhere herein to a patient in need thereof.

Provided herein is an antimicrobial agent as described anywhere herein for use in treating or inhibiting a genital bacterial infection and as a probiotic for maintaining a healthy genital microbiome. Also provided herein is an antimicrobial agent as described anywhere herein for use in treating or inhibiting a vaginal bacterial infection and as a probiotic for maintaining a healthy vaginal microbiome.

In some embodiments, the antimicrobial agent inhibits gram-negative bacteria such that the growth of the bacteria is reduced. In some embodiments, the antimicrobial agent inhibits gram-negative bacteria such that the bacteria are unable to form any CFUs. In some embodiments, the antimicrobial agent inhibits gram-negative bacteria such that the bacteria is killed. In some embodiments, the antimicrobial agent inhibits gram-negative bacteria such that the bacteria is completely absent. In some embodiments, the antimicrobial agent inhibits gram-negative bacteria below the symptomatic infection level for said bacteria. In some embodiments, the gram-negative bacteria is E. coli and the symptomatic infection level is measured as $10^5$ CFU/ml or more. In some embodiments, the gram-negative bacteria is a Pseudomonas species and symptomatic infection level is measured as $10^5$ CFU/ml or more. Thus, in some embodiments, the antimicrobial agent inhibits growth of gram-negative bacteria to less than $10^5$ CFU/ml. In some embodiments, the antimicrobial agent inhibits growth of E. coli to less than $10^5$ CFU/ml. In some embodiments, the antimicrobial agent inhibits growth of a Pseudomonas species to less than $10^5$ CFU/ml.

In some embodiments, the antimicrobial agent inhibits gram-negative bacteria and not gram-positive bacteria, such that the ratio of gram-negative bacteria to gram-positive bacteria is reduced compared to the ratio of said bacteria before exposure to the antimicrobial agent. In some embodiments, the antimicrobial agent inhibits E. coli. and not Lactobacillus species, such that the ratio of E. coli. to Lactobacillus is reduced compared to the ratio of said bacteria before exposure to the antimicrobial agent.

In some embodiments, the antimicrobial agent is for administration to a female subject. In some embodiments, the antimicrobial agent is for administration topically to a subject. In some embodiments the antimicrobial agent is administered to the external genital area, such as the vulva. In some embodiments, the antimicrobial agent is not for oral administration. The localised administration of the antimicrobial agent avoids complications of oral delivery routes, such as metabolic barriers and the effect of the gut.

3. The Formulation

Provided herein is a composition comprising an antimicrobial agent as described anywhere herein and one or more excipients. In some embodiments, the antimicrobial agent is Bdello, preferably Bdellovibrio bacteriovorus.

Also provided herein is a formulation comprising:
a. a composition comprising an antimicrobial agent as described anywhere herein and one or more excipients; and
b. one or more silicon-based polymers.

In some embodiments, the antimicrobial agent is Bdello. In some embodiments the antimicrobial agent is Bdellovibrio bacteriovorus.

In some embodiments, the one or more excipients comprise a bulking agent(s), stabiliser(s) and/or anti-caking agent(s). In some embodiments, the one or more excipients comprise one or more bulking agents and one or more stabilisers. In some embodiments, the one or more excipients comprise one or more bulking agents, one or more stabilisers, and one or more anti-caking agents.

In some embodiments, the bulking agent(s) is/are selected from one or more of sucrose, raffinose, trehalose, lactose, maltose, cellulose, mannitol, maize, corn, starch and maltodextrin. In some embodiments, the bulking agent comprises sucrose. In some embodiments, the bulking agent comprises lactose. In some embodiments, the bulking agent comprises sucrose and maltodextrin. In some embodiments, the bulking agent comprises lactose and maltodextrin.

In some embodiments, in the composition of (a), the one or more excipients comprise sucrose at about 1% w/v to 10% w/v including about 2% w/v, and maltodextrin at about 1% w/v to 10% w/w including about 2% w/v.

In some embodiments, the one or more excipients are selected from calcium salts and/or, magnesium salts. In some embodiments, the excipients comprise a calcium salt. In some embodiments, the calcium salt comprises $CaCl_2$. In some embodiments, the calcium salt comprises $CaCO_3$. In some embodiments, the excipients comprise a magnesium salt. In some embodiments, the magnesium salt comprises $MgCl_2$. In some embodiments, the magnesium salt comprises $MgCO_3$. In some embodiments, the stabilisers comprise $CaCl_2$ and $MgCl_2$. In some embodiments, the one or more excipients comprise calcium salts and/or magnesium salts, and bulking agent(s). In some embodiments, the one or more excipients comprise calcium salts and/or magnesium salts, and anti-caking agent(s). In some embodiments, the one or more excipients comprise calcium salts and/or magnesium salts, bulking agent(s) and anti-caking agent(s).

In some embodiments, the anti-caking agent(s) is/are selected from one or more of silicon dioxide, magnesium stearate and titanium dioxide.

In some embodiments, in the composition of (a), the one or more excipients comprise $MgCl_2$ at about 1 mM to 10 mM including at about 3 mM.

In some embodiments, the composition of (a) comprises the antimicrobial agent at <1% w/w. In some embodiments, the composition comprises the antimicrobial agent at about 1-5% w/w, including at about 2.5-3% w/w. In some embodiments, the composition comprises the antimicrobial agent at about 2.5-5% w/w. In some embodiments, the composition comprises the antimicrobial agent at about 2.5-8% w/w. In some embodiments, the composition comprises the antimicrobial agent at about 3% w/w. In some embodiments, the composition comprises the antimicrobial agent at about 5% w/w.

In some embodiments, the composition is freeze-dried and milled. In some embodiments, the composition is spray-dried and milled.

In some embodiments, the composition is combined with the one or more silicon-based polymers of (b) to produce the formulation.

In some embodiments, the formulation comprises less than 1% w/w water. In some embodiments, the formulation comprises no aqueous carrier system comprising water, such that the formulation is not water-based. In some embodiments, the formulation is silicon-based. In some embodiments the formulation is oil-based. In some embodiments, the formulation has low water activity. In some embodiments the formulation does not comprise preservatives. In some embodiments, the formulation does not comprise nanomaterials, such as nanoparticles.

In some embodiments, the formulation comprises one or more silicon-based polymers, such as dimethicones. In some embodiments, the formulation comprises a base formulation to which the antimicrobial agent and one or more excipients are added. In some embodiments, the base formulation comprises one or more silicon-based polymers. In some embodiments, the base formulation comprises one or more of SPECSIL K-17, VOLASIL DM-2, DIMETHISIL DM-5, COSMETIC FLUID 1406-OH and CRODAMOL IPM.

In some embodiment, the formulation comprises Bdello, one or more excipients, and one or more silicon-based polymers. In some embodiment, the formulation comprises Bdello, sucrose and maltodextrin, $MgCl_2$, and one or more silicon-based polymers. In some embodiments, the formulation comprises Bdello, sucrose and maltodextrin, $MgCl_2$, and SPECSIL K-17, VOLASIL DM-2, DIMETHISIL DM-5 and COSMETIC FLUID 1406-OH. In some embodiments, the formulation comprises 2-10% w/w Bdello composition (i.e. the Bdello, and the one or more or more excipients). In some embodiments, the formulation comprises 5% w/w Bdello composition. In some embodiments, the formulation comprises 3% w/w Bdello composition. In some embodiments, the formulation comprises about 5% w/w Bdello composition, 75% w/w SPECSIL K-17, about 19% w/w VOLASIL DM-2, about 0.75% w/w DIMETHISIL DM-5 and 0.25% w/w COSMETIC FLUID 1406-OH.

In some embodiments, the antimicrobial agent, composition, or formulation is formulated as a genital cream, for application to the external genital area as described herein. The genital cream is bioactive. In some embodiments, the cream is homogenous. In some embodiments, the genital cream is a vaginal cream.

In some embodiments, the antimicrobial agent, composition, or formulation is formulated into an applicator, for application to the external genital area as described herein. Examples an applicator include but are not limited to a wipe, sanitary pad or towel, gauze or cotton swab.

In some embodiments, the antimicrobial agent, composition, or formulation is formulated into a paste or gel, for application to the external genital area as described herein.

In some embodiments, the antimicrobial agent, composition, or formulation is formulated with any dermatologically acceptable carrier, i.e., a carrier that that is suitable for topical application to the external genital area.

The antimicrobial agent, composition, or formulation as described anywhere herein is a non-irritant, i.e., is suitable for application to sensitive skin.

In some embodiments, the antimicrobial agent, composition or formulation is administered once a day, twice a day, three times a day, or as needed by the subject. In some embodiments, the antimicrobial agent, composition or formulation is administered twice a day.

In some embodiments, a dose of $10^4$ PFU/per subject or more of the antimicrobial agent is administered per day. In some embodiments, a dose of $10^6$ PFU/per subject or more of the antimicrobial agent is administered per day. In some embodiments, the dose is $10^8$ PFU/per subject or more per day. In some embodiments, the dose is $10^{10}$ PFU/per subject per day. It will be understood that the dose refers to the dose of live predatory bacteria in the formulation.

In some embodiments, 8 grams or less of the formulation is administered to a subject per day. In some embodiments, 5 grams or less of the formulation is administered to a subject per day. In some embodiments, 1 gram of the formulation is administered to a subject per day, i.e. a dose of 1 g/day.

In some embodiments, at least 50 mg of the formulation is administered per unit of skin per day ($mg/cm^2/day$). In some embodiments, at least 70 mg of the formulation is administered per unit of skin per day ($mg/cm^2/day$). In some embodiments, at least 80 mg of the formulation is administered per unit of skin per day ($mg/cm^2/day$). In some embodiments, at least 90 mg of the formulation is administered per unit of skin per day ($mg/cm^2/day$).

In some embodiments, the antimicrobial agent, composition or formulation inhibits the growth of gram-negative bacteria 30 hours after administration. In some embodiments, the antimicrobial agent inhibits the growth of gram-negative bacteria 20 hours after administration. In some embodiments, the antimicrobial agent inhibits the growth of gram-negative bacteria 10 hours after administration.

In some embodiments, the formulation has a shelf-life of greater than 90 days, i.e. the antimicrobial agent retains its function of inhibiting gram-negative bacterial growth for over 90 days.

Provided herein is a pharmaceutical composition comprising a Bdello preparation and a pharmaceutically acceptable excipient.

4. Method of Manufacture

Provided herein is a method for manufacturing a composition comprising an antimicrobial agent as described anywhere herein, wherein the antimicrobial agent is:
  i) cultured
  ii) isolated
  iii) combined with one or more excipients, and
  iv) freeze-dried or spray-dried.

In some embodiments, the antimicrobial agent is Bdello, preferably *Bdellovibrio bacteriovorus*.

In some embodiments, the antimicrobial agent is co-cultured with non-pathogenic gram-negative bacteria host cells (prey).

In some embodiments, the gram-negative bacterial host cells are non-pathogenic *E. coli* cells, such as BL21 *E. coli* cells.

In some embodiments, the antimicrobial agent is Bdello and the non-pathogenic gram-negative bacterial host cells are *E. coli* cells.

In some embodiments, the gram-negative bacterial host cells and the antimicrobial agent are co-cultured until cell lysis of the gram-negative bacterial host cells occurs. In some embodiments, co-culturing comprises inoculating the gram-negative bacterial host cells with the antimicrobial agent, and incubating at about 30° C., 180 rpm for 24 to 120 hrs.

In some embodiments, after cell lysis, the cell mixture is cold incubated. This detaches the antimicrobial agent from the lysed gram-negative bacterial host cells. In some embodiments, the mixture is cold incubated for at least 30 minutes on ice or at or below 4° C.

In some embodiments, the cell mixture is centrifuged to separate and remove the lysed gram-negative bacterial host cells. In some embodiments, the cell mixture is filtered.

In some embodiments, the cell mixture is filtered to isolate the antimicrobial agent. In some embodiments, the cell mixture is filtered by a 1 μm filter, a 0.9 μm filter, a 0.8 μm filter, a 0.7 μm filter, a 0.6 μm filter or a 0.5 μm filter. In an embodiment, the cell mixture is filtered with a 0.45 μm filter.

In some embodiments, after co-culturing and before freeze-drying or spray-drying, the antimicrobial agent is stored at 4° C.

In some embodiments, after co-culturing and before freeze-drying or spray-drying, the antimicrobial agent is purified and/or concentrated.

In some embodiments, wherein the antimicrobial agent is Bdello, the Bdello for co-culturing is isolated from soil or water sources, such as rivers, lakes, seawater, marine sediments and sewage. In some embodiments, the Bdello is isolated from filtered soil samples. In some embodiments, the Bdello is isolated from filtered water samples. In some embodiments, Bdello is isolated as a DNA sample. Bdello is then produced by replicating said DNA and culturing bacteria produced from said DNA, according to any known methods in the art, such as via a bioreactor.

After isolation, the composition is combined with one or more excipients. Said excipients may be as defined anywhere herein. In some embodiments, one or more excipients are added to the composition after the freeze-drying or spray-drying process.

In some embodiments, in step (iv), the composition is freeze-dried. In some embodiments, in step (iv), the composition is spray-dried.

In some embodiments, the isolated Bdello is combined with the one or more excipients by gentle mixing.

In some embodiments, after the freeze-drying or spray-drying, the agent is further processed to reduce the particle size of the agent and produce a homogenous mixture of particles. In some embodiments the agent is milled. In some embodiments, the post-processed agent has a particle size of 5 to 10 microns.

In some embodiments, the method further comprises formulating the composition into a formulation as described anywhere herein. In some embodiments, the method further comprises combining the composition with one or more silicon polymers.

In some embodiments, preparation of the formulation comprises:
  a) pre-mixing the composition with a silicon compound
  b) gently stirring the mixture from step a) with a further silicon compound, and
  c) gently stirring the mixture from step b) with a silicon mixture.

In some embodiments, preparation of the formulation comprises:
  a) pre-mixing the composition with VOLASIL DM-2
  b) gently stirring the mixture from step a) with SPECSIL K-17 until uniform, and
  c) gently stirring the uniform mixture from step b) with a mixture comprising VOLASIL DM-2, DIMETHISIL DM-5 and COSMETIC FLUID 1406-OH until uniform.

EXAMPLES

Example 1

Figure 2:
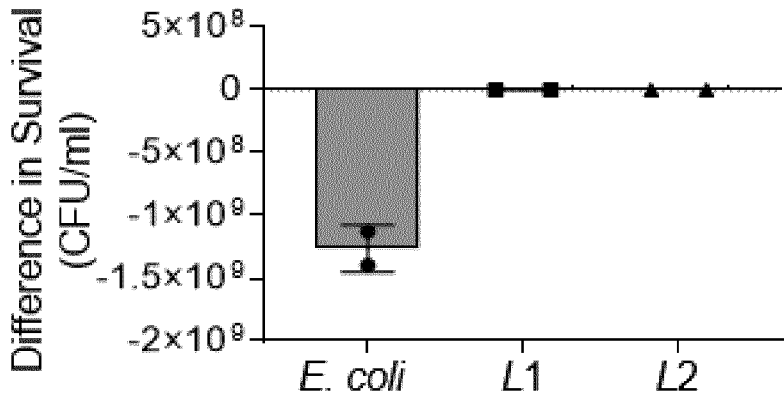
FIG. 2. The number of *E. coli* colonies was greatly reduced following 24 h incubation with *B. bacteriovorus*, compared to *E. coli* in the absence of *B. bacteriovorus* (mean 283.34 and $1.24 \times 10^9$ cfu/ml, respectively). There was little difference in the number of probiotic *Lactobacillus* spp. colonies (L1 and L2) with or without *B. bacteriovorus* (L1: mean $1.8 \times 10^2$ and $3.8 \times 10^2$ cfu/ml, respectively; L2: mean $1 \times 10^4$ and $7 \times 10^4$ cfu/ml, respectively).
L1: commercial probiotic containing *L. plantarum* P-17630
L2: commercial probiotic containing *L. rhamnosus* GR-1 and *L. reuteri* RC-14
Figure 3:
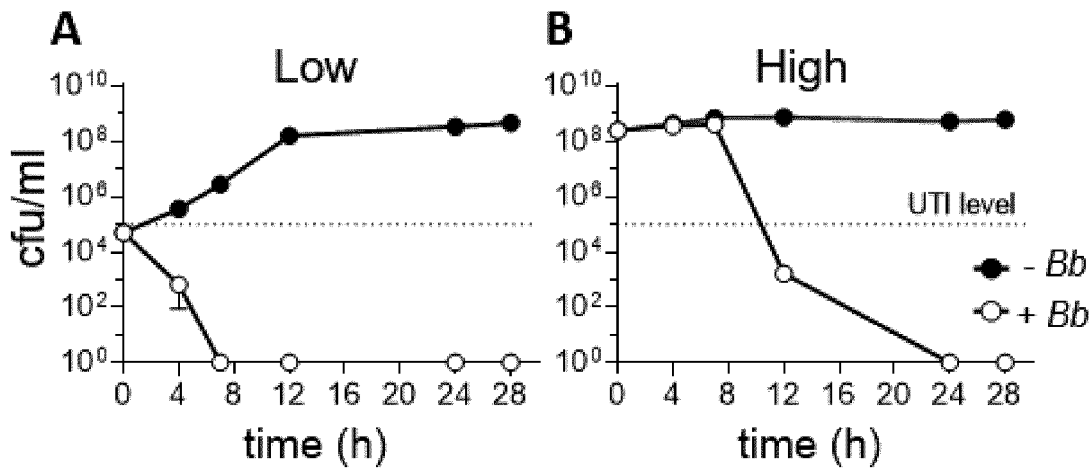
FIG. 3. A high inoculum of *B. bacteriovorus* (approx. $10^8$ pfu/ml) efficiently killed *E. coli* at both low (A) and high (B) initial infection levels. Prey was enumerated by CFU counts throughout. (A) An initial *E. coli* level of <$10^5$ cfu/ml never rose above UTI level ($10^5$ cfu/ml indicated by dotted line) and was undetectable by T8. (B) An initial high level of *E. coli* was reduced below UTI level within 12 h and was undetectable by T24.
Limit of detection=100 cfu/ml
Bb: *B. bacteriovorus*
Figure 4:
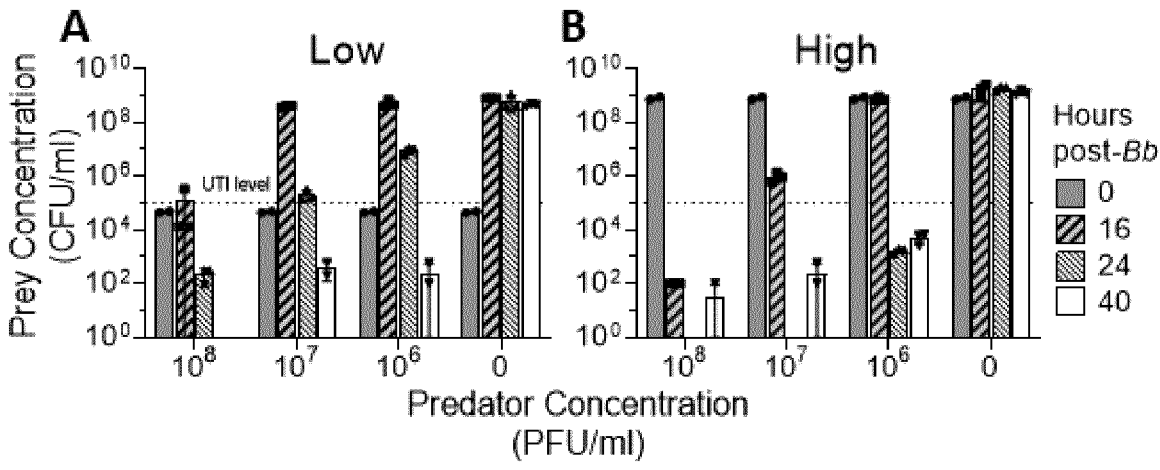
FIG. 4. Low (A) and high (B) initial infection levels of *E. coli* were incubated with decreasing doses of *B. bacteriovorus* (predator) and monitored for survival/growth over time. In both cases, a high predator concentration of at least $10^8$ pfu/ml was efficient at suppressing *E. coli* at or below UTI level ($10^5$ cfu/ml, indicated by dotted line), whereas lower predator inocula ($10^7$ and $10^6$ pfu/ml) allowed for proliferation of *E. coli* above UTI level until 24-40 h post-*B. bacteriovorus*.

Prey/Probiotic Susceptibility to *B. bacteriovorus*
  1. *E. coli* and *Pseudomonas* strains were grown in LB. Lactobacilli from commercial probiotics were grown in MRS broth.
  2. Prey was grown to $OD_{600nm}=2$ in appropriate media, pelleted by centrifugation at 4,000 rpm for 20 min at 4° C., and resuspended in an equal volume of dilute nutrient broth (DNB). For low prey inocula, *E. coli* was further diluted 1:1000 in DNB.
  3. It was then transferred to replicate wells of a 24-well plate and *B. bacteriovorus* lysate was added at the desired ratio of infection (mean ROI of Gram-negative lysis assays (FIG. 1)=1:60, mean ROI of probiotics lysis assays (FIG. 2)=1:19).
  4. *B. bacteriovorus*-free control wells were included with DNB added in place of lysate.
  5. Plates were incubated at 37° C. in a microplate reader and the absorbance at 600 nm measured periodically over 24-30 hours. Absorbance values were determined by subtracting the absorbance of media-only blanks (FIG. 1A, C).
  6. Live prey bacteria were enumerated at T0 and T24 by plating serial dilutions and counting colony forming units (FIG. 1 B, D; FIG. 2, 3, 4).

Example 2

Testing Stability of Lyophilised *B. bacteriovorus*
  1. *B. bacteriovorus* lysate was generated in co-culture with *E. coli* (detailed in Example 4, below).
  2. The lysate was filtered through a 0.45 μm membrane before combining with excipient stocks. A small sample was kept to test pre-lyophilisation abundance and the remainder was freeze-dried.

3. The lysate was serially diluted in PBS and 100 µl of each dilution was added to 400 µl *E. coli* in yeast-peptone (YP) broth at a concentration of $10^{10}$ cfu/ml. This was incubated at 30° C. for 30 min.

4. The predator-prey mix was then combined with 4 ml YP Top Agar (0.6% agar) and spread over dry YP Bottom Agar (1.9% agar) plates.

Figure 5:
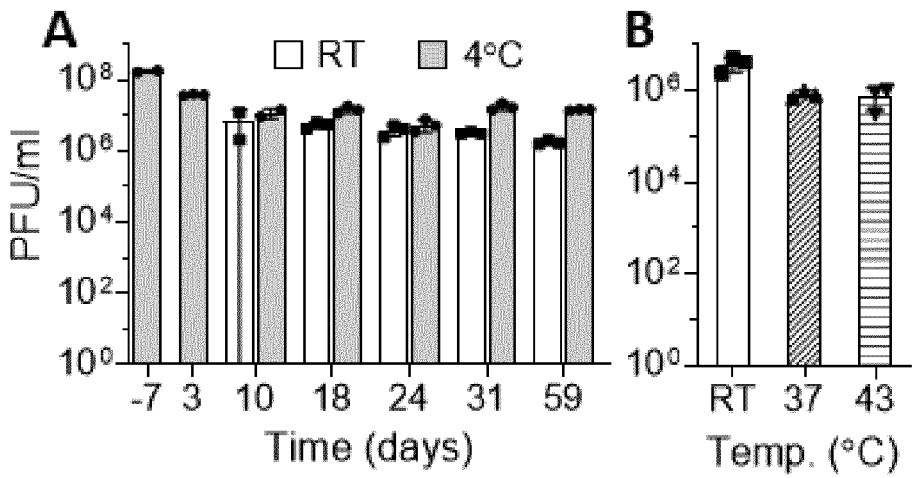
FIG. 5. The stability of lyophilized *B. bacteriovorus* was tested at various temperatures. (A) & (C) Lysate was plated for plaque-forming units (PFU) prior to lyophilization (day −7), upon receipt following lyophilization (day 3), and periodically thereafter. Lyophilised samples were stored at room temperature (RT) or 4° C. (B) On day 23, triplicate samples from RT storage were transferred to 37° C. or 43° C. They were plated for PFU counts after 24 h at these elevated temperatures.
Figure 5:
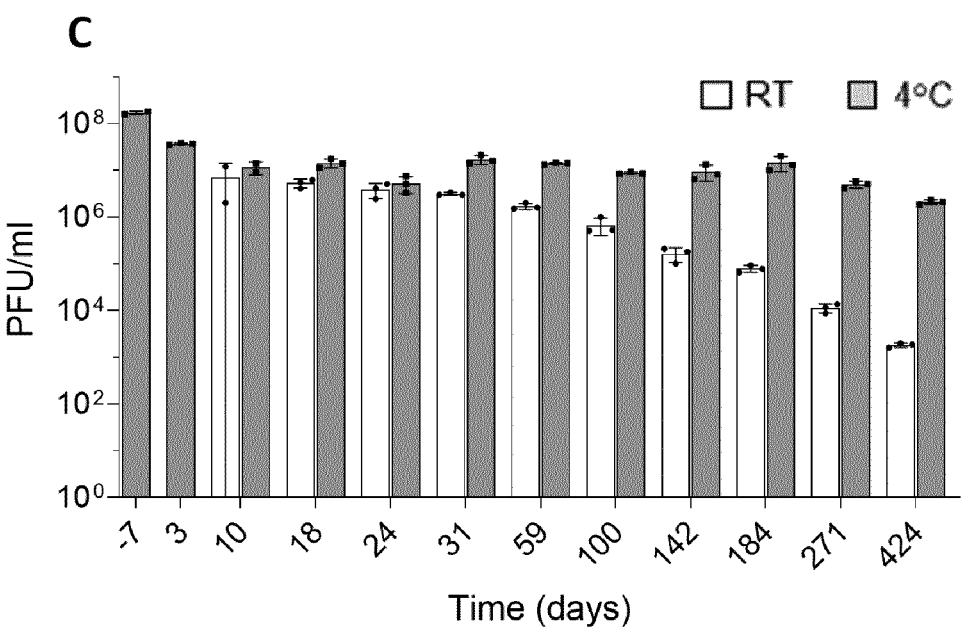

5. Plates were left to dry and then incubated at 30° C. for up to 3 days until plaque-forming units (PFU) were clear and could be counted (FIGS. 5A & C).

6. Upon receipt of 1 ml bottles of the lyophilized *B. bacteriovorus,* 3 were rehydrated with sterile distilled water and plated for PFU counts to determine loss due to the freeze-drying process.

7. Half of the sample bottles received were stored at room temperature (RT) and half at 4° C.

8. Triplicate samples from both temperatures were periodically rehydrated and plated for PFU counts to determine if there was loss of activity over time.

9. On day 23 post-lyophilisation, triplicate RT samples were stored at 37° C. or 43° C. for 24 h. They were then rehydrated and plated for PFU counts to determine if they could survive at these elevated temperatures (FIG. 5B).

Example 3

Tolerance Testing of Lyophilised *B. bacteriovorus* in a Silicon-Based Cream

1. Lyophilised *B. bacteriovorus* was ground to a fine powder before stirring into a silicon-based formulation resulting in a cream containing predator at a concentration of approx. $1.6 \times 10^5$ pfu/g.

2. A small aliquot of this, approx. 100 µl, was dropped into triplicate 10 ml *E. coli* cultures in DNB.

3. These were incubated at 37° C., 180 rpm and monitored for lysis of the *E. coli*.

Figure 6:
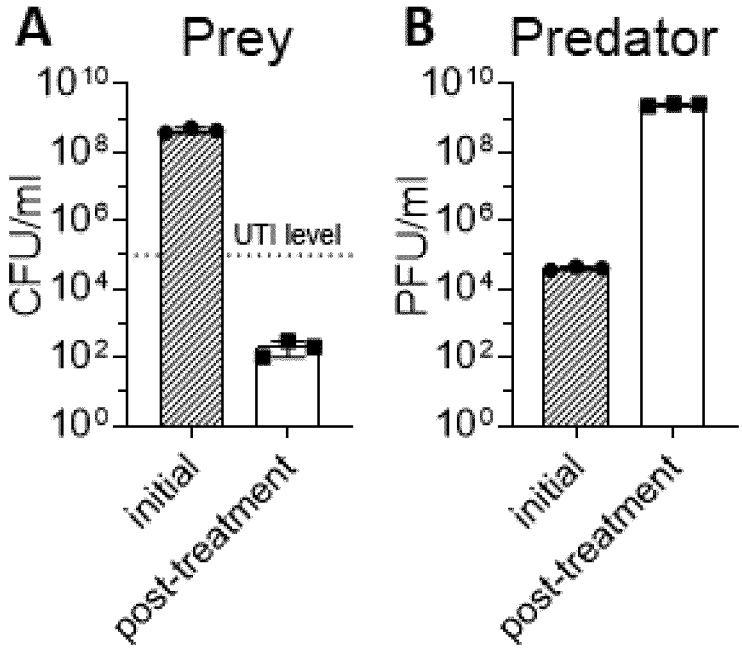
FIG. 6. *B. bacteriovorus* was mixed with a silicon-based cream and inoculated into an *E. coli* (prey) culture. Following incubation, *E. coli* had reduced below UTI level ($10^5$ cfu/ml, indicated by dotted line (A)), and *B. bacteriovorus* (predator) had proliferated to >$10^9$ pfu/ml (B).

4. Once lysis had occurred, the resulting lysate was plated for CFU counts to determine the reduction in *E. coli* due to activity of the predator (FIG. 6A).

5. The lysate was then harvested and plated for PFU counts, confirming that *B. bacteriovorus* had escaped from the cream and successfully proliferated in the prey culture (FIG. 6B).

Example 4

Exemplary Method of Manufacture

Upstream

1. Preparation of the prey and media exchange: *E. coli* cells were grown in LB (50-500 ml) and grown to $OD_{600nm}=2$. The cells were collected by centrifugation at 4,000 rpm for 20 min, 4° C. and resuspended in an equal volume of fresh DNB medium.

2. Preparation of the predator inoculum: Frozen stock of *B. bacterivorous* was inoculated into a 50 ml *E. coli* culture ($OD_{600nm}=2$). Following lysis of the *E. coli*, the cells were enumerated by plating for PFUs and used as the predator inoculum.

3. Prey-predator co-culture: *B. bacterivorous* was inoculated into the DNB medium containing prey (step 1) at a specific Ratio of Infection. (1:50-1:100 (predator: prey)). The cells were co-cultured at 30° C., 180 rpm for 24-72 hrs. In order to determine when lysis had occurred, OD was monitored periodically until it dropped to approx. 0.6-0.4.

Downstream

1. Detachment of predator from prey: The co-culture was incubated on ice or at 4° C., for at least 30 min.

2. Removal of prey cell debris: *E. coli* cell debris was removed by centrifugation at 2500×g for 15 min, 4° C.

3. Filtration: For further removal of the prey, the supernatant containing predator from step 2 was filtered through a 0.45 µm filter membrane.

4. Freeze-drying: Predator was freeze dried and stored for further applications.

Example 5

User Investigation Evaluating the Effect of a Cosmetic Ingredient to Maintain and Protect the Female Intimate Microbiome Method 1. Eleven healthy female volunteers were recruited and consented to take part in the study. They were not pregnant, suffering from any infections, or taking any antibiotics.

2. All participants were sent a study kit containing the following: 2× spray bottles of the active *B. bacteriovorus* (up to $1.9 \times 10^8$ bacteria/ml) in PBS, 35× individually-wrapped sterile pieces of non-absorbent cotton wool, 2× Women's Complete MicrogenDX microbiome kits, vaginal pH test strips, instruction manual.

3. Participants were instructed to refrain from using soaps or other intimate products for a minimum of 5 days prior to starting the application period. They were instructed to use only warm water to wash their external genitalia.

4. Following this "wash in" period, they were instructed to use one of the Women's Complete MicrogenDX microbiome kits to collect a urine sample and vaginal swabs. This would indicate their baseline microbiota.

5. The application period lasted 7 days and, during this time, participants applied approx. 1 ml of the solution to their external genitalia morning and night.

6. After the 7 application days each participant used the remaining Women's Complete MicrogenDX kit to collect another urine sample and vaginal swabs.

7. All urine and vaginal samples were sent to MicrogenDX for analysis. All samples were screened by both quantitative polymerase chain reaction (qPCR) for a range of specific bacteria, and next generation sequencing (NGS) of the 16S rRNA gene using primers targeting the V1-V2 hypervariable region.

8. Specific organisms quantified by qPCR in urine samples were: *Mycoplasma hominis, Enterococcus faecalis, Streptococcus agalactiae, Klebsiella pneumoniae, Staphylococcus aureus, Escherichia coli, Gardnerella vaginalis, Mobiluncus curtisii, Mobiluncus mulieris, Prevotella bivia, Ureaplasma urealyticum, Ureaplasma parvum, Candida albicans.*

9. Specific organisms quantified by qPCR in vaginal samples were: *Mycoplasma hominis, Streptococcus agalactiae, Gardnerella vaginalis, Mobiluncus curtisii, Mobiluncus mulieris, Prevotella bivia, Ureaplasma urealyticum, Ureaplasma parvum, Lactobacillus gasseri, Lactobacillus crispatus/acidophilus, Candida albicans.*

10. Bacterial presence and/or abundance was compared pre- and post-application by analysing both qPCR and NGS data provided by MicrogenDX. Note that absolute abundance via qPCR could not be reported for vaginal samples, due to them not being liquid samples, and are instead reported as none, low, medium or high abundance.

Results

1. Two participants withdrew from the study. One got an infection in the preparation period, prior to the study and so was no longer eligible to take part. Another got a long awaited appointment that would interfere with the study and we decided to withdraw her. Both withdrawals were unrelated to the test solution.

2. Note that for NGS analysis, only taxa that made up at least 2% of the total sequences were reported by MicrogenDX.

3. Urine samples:

Two common UTI pathogens, *E. faecalis* and *E. coli*, had reduced abundance as determined by targeted qPCR (FIG. 7A, 7B). Three individuals gained commensal lactobacilli, with four others retaining the lactobacilli that were present pre-application (FIG. 7C). Relative abundance of *Lactobacillus* spp. was determined by NGS of 16S rRNA. One participant had *Klebsiella pneumoniae* pre-application that was not detected post-application (data not shown). *Enterobacter cloacae* and *Citrobacter freundii* were detected by NGS in two different individuals pre-application and were undetectable post-application.

4. Vaginal samples:

*Gardnerella vaginalis* was detected by targeted qPCR in five samples pre-application, with two (40%) of those having none post-application (data not shown). *Ureaplasma parvum* was lost in one participant and *Mobiluncus curtisii* in another, both detected by targeted qPCR. Note that only a rough abundance (low, medium, high) was reported for vaginal qPCR samples due to them being solid samples, so DNA copies/ml could not be determined. We therefore report changes in presence/absence of specific bacteria rather than absolute abundance. Lactobacilli were detected in almost all samples (89%, n=8) pre-application by qPCR and/or NGS. All of these individuals retained these lactobacilli by the end of the study.

5. Across all samples, we saw a reduction in a wide range of pathogens, including Gram-positive and Gram-variable organisms. Many of these lack a typical cell wall, eg. *G. vaginalis* has a thin cell wall, *E. faecalis* can exist in a cell wall-free state called L-form. These abnormal cells may be more susceptible to predation by *B. bacteriovorus* compared to normal Gram-positive bacteria. *B. bacteriovorus* may also disrupt biofilms of Gram-positive bacteria, making them more susceptible to killing by host immune cells.

Figure 8:
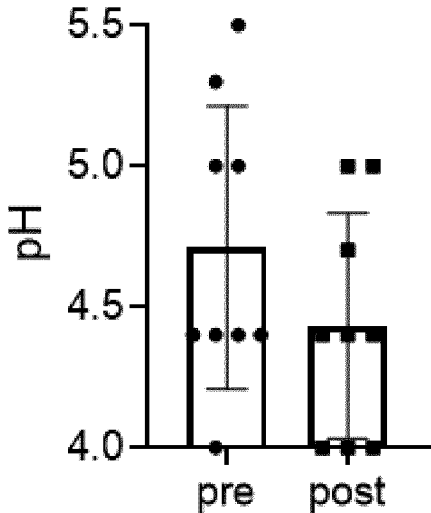
FIG. 8. There was an overall reduction in vaginal pH in the study participants following application of *B. bacteriovorus*.

6. There was an overall reduction in vaginal pH following the application period. Average initial pH=~4.7, average post-application=~4.4 (FIG. 8).

Example 6

A Test Product, Active *B. bacteriovorus* in PBS, was Tested for its Activity on Human Vaginal Tissue Colonized with *Lactobacillus acidophilus* and/or *Escherichia coli*

Reconstituted human vaginal epithelium (HVE) model colonised with *Lactobacillus* sp. recapitulates the in vivo vaginal epithelium and its commensal flora allowing a more realistic and relevant model in terms of physiological response to topical treatments and hygienic procedures. Lactobacilli belong to the commensal gastrointestinal and urogenital microbiota of man and animals and are considered protective organisms, able to inhibit growth of pathogenic organisms by production of antimicrobial molecules and a low pH environment. The low pH environment is considered a result of microbial metabolic products of glycogen (mostly lactic acid) which is produced by vaginal epithelial cells.

Method

1. Human vaginal epithelium (HVE) inserts were maintained according to manufacturer instructions (Episkin).

2. *L. acidophilus* and/or *E. coli* were added to the tissues in the absence of *B. bacteriovorus* in order to establish the baseline colonisation levels of the bacteria.

3. In a test plate, *L. acidophilus* and *B. bacteriovorus* were co-inoculated onto the tissue. Following a 16 h colonisation period, uropathogenic *E. coli* was added for 4 hours.

4. All HVE plates were incubated at 37° C., 5% $CO_2$ for the duration of the experiment.

5. *L. acidophilus* was recovered from the tissue at T20 and enumerated by plating serial dilutions on selective media.

6. The abundance of bacteria following infection was compared to colonisation in the control plate in order to determine survival or growth.

Results

Figure 9:
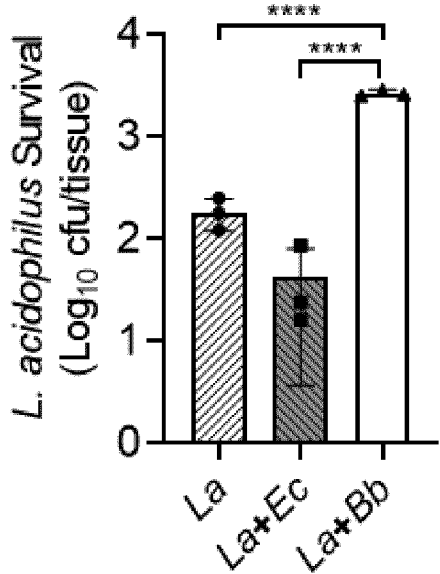
FIG. 9. There was significantly more colonising *L. acidophilus* at 20 hours following concurrent pre-treatment with *B. bacteriovorus*, p=0.0342.

Pre-treatment of HVE with active *B. bacteriovorus* with concurrent *L. acidophilus* colonisation, followed by *E. coli* addition, resulted in an increased abundance of *L. acidophilus*, p=<0.0001 determined by unpaired t test (FIG. 9).

The *E. coli* strain failed to colonise this tissue in the control plate. Therefore no conclusions could be drawn regarding its abundance following co-incubation with *B. bacteriovorus*.

Example 7

A 96-Hour Patch Test to Determine the Cutaneous Irritancy of a Cosmetic Products in a 25 Volunteer Panel Summary A cosmetic product and a negative control were tested for their potential to cause cutaneous irritancy in a test panel of 27 non-patient volunteers. The design of the study was that of a 96-hour occluded patch test. In such a design, test products were applied to test sites on the skin of the upper arm under occlusion for four consecutive periods of 24 hours (+/−1 hour) with assessments at 24, 48, 72 and 96 hours post-application. The primary marker of cutaneous irritancy was considered to be erythema which was graded using a 0-6 ranking scale. Using this scale, a grade 2 reaction (moderate, uniform erythema) was considered a significant indication of cutaneous irritancy.

The results of the study are summarized as follows:

No grade 2 or higher reactions were recorded with *Bdellovibrio bacteriovorus* in PBS during the study. Three grade 1 reactions were recorded with *Bdellovibrio bacteriovorus* in PBS during the study. This result indicates that *Bdellovibrio bacteriovorus* in PBS may be classified as a Non-irritant under the conditions of this test.

Objectives

To determine the cutaneous irritancy of a cosmetic product and a single control product in 27 non-patient volunteers.

Study Design

The study was an open study of a skincare product in 27 volunteers. Each volunteer received a cosmetic product and a single control to the designated sites on the upper arm for 96 hours (four consecutive 24 hour applications to the same site). Products were applied using occlusive 12 aluminium Finn Chambers®.

Following test chamber removal, the test sites were wiped with a gauze swab to remove residual test product prior to assessment for skin reactions using 0-6 ranking scales for erythema and descriptive clinical terms. If no significant cutaneous irritation is observed, products were applied at 24, 48 and 72 hours post initial application. Volunteers returned to the clinic for final assessments at 96 hours post initial application.

Study Schedule

The products were in continuous contact with the skin of the upper arm over a 96-hour period. The test products were applied and removed, and the sites assessed using the following schedule:

| Day 1 | Mon | Apply materials under occlusion. | |
|-------|-----|----------------------------------|---|
| Day 2 | Tues | Remove, wait a minimum of 10 min. Assess sites | Re-apply |
| Day 3 | Weds | Remove, wait a minimum of 10 min. Assess sites | Re-apply |
| Day 4 | Thurs | Remove, wait a minimum of 10 min. Assess sites | Re-apply |
| Day 5 | Fri | Remove, wait a minimum of 10 min. Assess sites. End of Study. | Not reapplied |

Materials

The test materials were as follows:

| Sample | Product | Description |
|--------|---------|-------------|
| A | Cosmetic | *Bdellovibrio bacteriovorus* in PBS |
| C | Control | 11 mm Filter paper disc wetted with 0.05 ml of 0.9% saline |

Test material A was supplied by the Sponsors and was stored in the fridge between 4-8 C. The 12 aluminium Finn Chambers® and 11 mm filter paper discs (obtained from Biodiagnostics, www.biodiagnostics.co.uk) and Saline will be supplied by Cutest.

Sample Preparation

A sufficient amount (approx. 50 ul) of each sample was dispensed into a 12 aluminium Finn Chamber®. Samples were applied to the upper arm using 12 mm Finn Chambers® on Scanpor® tape. An 11 mm filter paper disc was included into the Finn Chamber® if required.

Test Sites

Figure 10A:
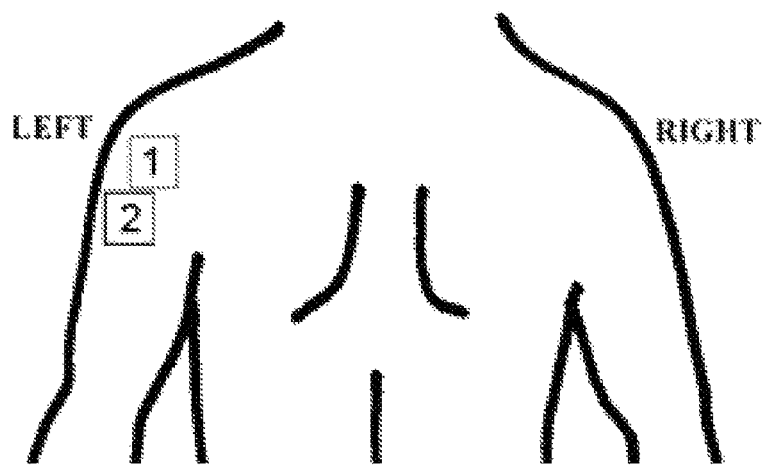
FIGS. 10. (A) and (B) show the test site for the irritancy study was the upper arm. The test material and the control were applied to either the left or right upper arm.
Figure 10B:
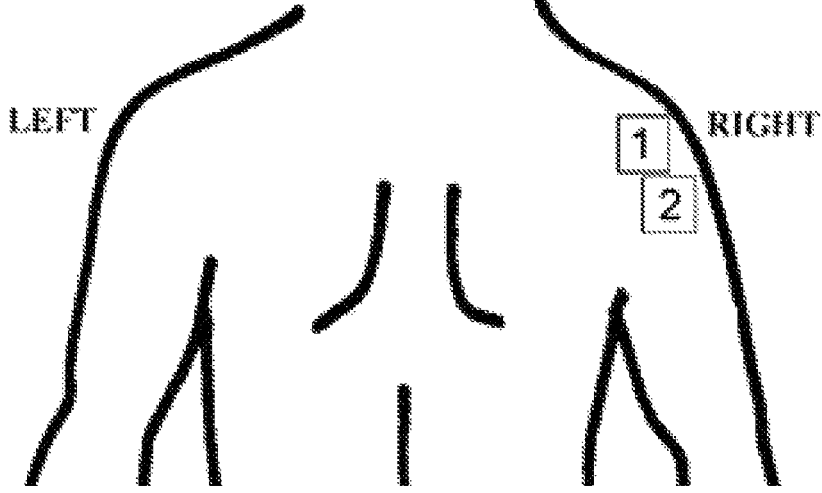

The test site for the irritancy study was the upper arm. The test material and the control were applied to either the left or right upper arm as shown in FIGS. 10a and 10b:

The allocation of products to test sites 1 to 2 corresponded to products A-B, respectively. The test sites were not specifically cleaned prior to test product application. The test sites were inspected for any features such as moles or blemishes and the test products applied in such a way as to avoid covering such features.

Test chambers were carefully removed and the test sites were wiped with a gauze swab to remove any remaining test product. The sites were assessed after a minimum of 10 minutes to allow any tape reactions to subside. Volunteers were requested not to interfere with the test sites during this time.

Volunteers

'Admission to Study' procedures were followed as outlined in the study protocol. All volunteers fulfilled the inclusion and exclusion criteria as detailed below:

Inclusion Criteria:

1. Volunteers who are aged 18-75 years.
2. A minimum of 50% of Volunteers with self-reported sensitive skin as determined by sensitive skin selectivity questionnaire.
3. A minimum of 50% Volunteers with self reported normal skin.
4. Volunteers who are healthy with no significant concurrent illnesses or skin disease.
5. Volunteers who have signed the consent form after the nature of the study has been fully explained.
6. Volunteers who have not travelled outside the UK in the last two weeks.
7. Volunteers who are able to attend all scheduled visits.

Exclusion Criteria:

1. Females who are pregnant, breast feeding, lactating or have given birth within the previous 6 weeks or are planning to become pregnant during the study
2. Volunteers who take any systemic or topical medication likely to interfere with the study e.g. anti-inflammatory drugs such as systemic steroids.
3. Volunteers who have taken part in a Health Research Authority or MHRA regulated clinical trial (e.g. at a hospital or phase I unit) within the previous eight weeks. Volunteers who have taken part in a study involving the test site during the previous four weeks.
4. Volunteers with a recent history (previous 12 months) of significant skin disease requiring medical intervention, e.g. Dermatology outpatient appointment. Volunteers with a proven allergy to cosmetic products or cosmetic ingredients likely to interfere with the study.
5. Volunteers who currently have symptoms associated with Covid19 (high temperature, a new continuous cough, loss or change in sense of taste and smell), those who have been advised to shield during the pandemic or advised to self-isolate.

Volunteer Restrictions

Volunteers were requested not to spend prolonged periods in the bath, go swimming or use saunas/steam rooms. They were also requested to avoid any exercise which may lead to heavy perspiration and to avoid scratching the test sites. Volunteers were requested to avoid sunbathing and use of sunbeds.

Medical History

All volunteers were non-patient volunteers who had previously undergone a medical examination before joining the test panel. Each volunteer's medical history was also updated and recorded immediately prior to participation in this study by the study nurse.

Assessments

Test Patch Adhesion

To assist in assessing product contact with the skin, the adhesion of the patches was recorded at each visit, prior to the removal of the test chambers using a five-point ranking scale as follows:

| 0 | = | >90% (essentially no detachment of Scanpor ® tape). |
| 1 | = | 75% to <90% adhered (some edges of Scanpor ® tape detached from the skin, chamber not affected). |
| 2 | = | 50% to <75% adhered (up to half the Scanpor ® tape detached, test site not occluded) |
| 3 | = | <50% adhered (Scanpor ® tape more than half detached) |
| 4 | = | Test product fully detached |

Erythema

At each assessment time the sites were graded for on a published 1 0-6 ranking scale as follows:

0=No reaction.

0.5=Slight, patchy erythema

1=Slight uniform erythema

2=Moderate, uniform erythema

3=Strong erythema

4=Strong erythema, spreading outside patch

5=Strong erythema, spreading outside patch with either swelling or vesiculation

6=Severe reaction with erosion

Clinical Signs

The following letters were appended to the numerical erythema score if a clinical sign was noted at the test site:

OE=Oedema

V=Vesiculation

S=Scaling

C=Cracking or crazing

SC=Scabbing

P=Papules

SO=Reaction spreading outside area of application

G=Glazing

N=None

These observations were for additional information only and did not influence the assessment of irritancy which is based on erythema scores alone.

Subjective Comments

The letters BS (Burning or Stinging) were appended to the numerical score if reported by the volunteers.

Statistical Considerations

Grading system for degree of irritancy (25 Volunteer Panel)

The category of irritant is determined primarily by the number of grade 2 or greater reactions that occur during the application period (Column A).

The category of irritant may be increased to a higher one if the number of volunteers reacting with a grade 1 reaction at the end of the study exceeds the total number of reactions for that category description.

Grade 0.5 reactions are for information only and do not affect the category of irritancy.

| Column A No. of volunteers reacting with a grade 2 or more reaction during the application period. | Column B No. of volunteers reacting with a grade 1 reaction at the end of the study. | Column C Total number of reactors. Column A plus Column B. | Category of irritant. |
| --- | --- | --- | --- |
| None | 1 volunteer | 1 volunteer or less | Non-irritant |
| 1 volunteer | Up to 2 volunteers | 1-3 volunteers | Weak |
| 2 volunteers | Up to 3 volunteers | 2-5 volunteers | Mild/moderate |
| 3-4 volunteers | Up to 6 volunteers | 3-10 volunteers | Moderately strong |
| 5-9 volunteers | Up to 10 volunteers | 5-19 volunteers | Strong |
| 10-25 volunteers | Up to 15 volunteers | 10-25 volunteers | Very strong |

Results

Demographics

Enrolled: 27 volunteers

Age range/Mean: 24 years-74 years, 47 mean years

Gender: 23 female, 4 male

Data exclusions: One data exclusion occurred where the adhesion score was graded 4. According to the test patch adhesion scale, the test product would have become fully detached prior to removal at the clinic and therefore any erythema observed may not be clearly attributable to the product.

Volunteer 08, Product A

Protocol Deviations

Two protocol deviations occurred during the study.

Volunteer 25 removed their own patches on the $30^{th}$ November for an MRI scan, the volunteer attended clinic straight after to have patches reapplied.

Volunteer 03 had skin assessments 1 hour and 2 minutes outside of the 24 hour (+/−1 hour) tolerance.

Volunteer Withdrawals

One volunteer was withdrawn from the study due to an adverse event.

Serious Adverse Events (SAE)

No SAE's were reported during the study.

Comments

Test Patch Adhesion

The test patches were assessed for adhesion at each visit. Overall, all scores (312 out of 314 assessments, 99.4%) were grade 1 or grade 0 and indicating excellent contact between the skin and the test products.

*Bdellovibrio bacteriovorus* in PBS

No grade 2 reactions or higher reactions were recorded with *Bdellovibrio bacteriovorus* in PBS during the study. Three grade 1 reactions were recorded with *Bdellovibrio bacteriovorus* in PBS during the study. This result indicates that *Bdellovibrio bacteriovorus* in PBS during may be classified as a Non-irritant under the conditions of this test.

11 mm Filter Paper Disc Wetted with 0.05 ml 0.9% Saline Solution (Control)

No grade 2 reactions or higher reactions were recorded with 11 mm Filter paper disc wetted with 0.05 ml 0.9% saline solution (control) during the study. One grade 1 reaction was recorded with 11 mm Filter paper disc wetted with 0.05 ml 0.9% saline solution (control) during the study.

Summary Findings

The results of this 96-hour occluded patch test demonstrate that the *B. bacteriovorus* test product elicited only very low levels of irritation in a mixed panel of volunteers of whom 50% were sensitive skin type. The *B. bacteriovorus* was therefore well tolerated and the claims of dermatologically tested and suitable for sensitive skin can be supported.

In conclusion, based on the results of the study, the product tested may be considered dermatologically approved and highly unlikely to cause significant skin irritation under normal intended use.

Summary of Erythema Scores

| Product | Grade of Reaction | 24 Hours | 48 Hours | 72 Hours | 96 Hours |
|---|---|---|---|---|---|
| *Bdellovibrio bacteriovorus* in PBS | | | | | |
| A | No. grade 0 | 15 | 16 | 16 | 19 |
| No. grade 0.5 | | 9 | 10 | 9 | 7 | 7 |
| No. grade 1 | | 2 | 0 | 1 | 0 | 0 |
| No. grade 2 | | 0 | 0 | 0 | 0 | 0 |
| No. grade >2 | | 0 | 0 | 0 | 0 | 0 |

-continued

| Product | Grade of Reaction | 24 Hours | 48 Hours | 72 Hours | 96 Hours |
|---|---|---|---|---|---|
| No. of NR | | 0 | 0 | 0 | 0 | 0 |
| 11 mm Filter paper disc wetted with 0.05 ml of 0.9% saline solution | | | | | |
| B | No. grade 0 | 21 | 22 | 21 | 23 |
| No. grade 0.5 | | 6 | 4 | 4 | 3 | 3 |
| No. grade 1 | | 0 | 0 | 1 | 0 | 0 |
| No. grade 2 | | 0 | 0 | 0 | 0 | 0 |
| No. grade >2 | | 0 | 0 | 0 | 0 | 0 |
| No. of NR | | 0 | 0 | 0 | 0 | 0 |

In conclusion, these Examples demonstrate that the antimicrobial agent of the present invention is able to re-build or maintain a healthy genital microbiome. Thus, the antimicrobial agent of the present invention is microbiome friendly, and is a microbiome strengthening solution.

Example 8

Study Design to Evaluate the Impact of a Bdello Cosmetic Topical Cream for Intimate Application on Vaginal Microbiome in Postmenopausal Women The study will be performed in an open-label design with a 1-week lasting run-in period (basal characterization of subjects with regard to vaginal pH-value), followed by a 3-week lasting intervention period. During baseline and end of intervention vaginal flora and urine microbiome will be determined and changes over time will be investigated. To estimate sustainability of study product on vaginal flora, a follow up phase of 2 weeks is proposed.

Thus, inter-individual variability will be diminished as the product effect on vaginal pH, as well as on microbiome data will be compared intra-individually with the respective status during the run-in period. An application period of 3 weeks should be sufficient to assess the efficacy of the current study product.

Pre-Selection Period:

45 subjects will be recruited based on their history of recurrent urinary tract infections and symptoms. After informed consent, subjects will be screened for their eligibility. If all eligibility criteria are met, subjects will be thoroughly instructed how to collect the samples for vaginal microbiome and urine microbiome analysis (qPCR and 16S-rRNA analysis), pH measurements and urine for urinalysis with dip stick.

As a next step of the pre-selection period from these 45 subjects, qPCR analysis for gram-negative bacteria and total bacteria will be performed in vaginal swabs. 30 subjects with the highest amounts of gram-negative bacteria will be finally selected for the clinical study.

Study Design:

Non-randomised, open-label, single-centre, pilot study

Test Products (Dose and Mode of Administration):

Bdello cream application. The cosmetic cream will be applied topically, twice daily Duration of Intervention:

21 days. The study will consist of a screening visit, including a pre-selection approach based on gram-negative bacteria measured with qPCR, a 1-week run-in phase, a 3-week intervention phase and a 2-week follow up phase Number of Subjects (Planned):

30 subjects out of 45 pre-selected subjects.

25

Main Criteria for Inclusion:

(1) Postmenopausal women suffering from recurrent urinary tract infections (defined as two episodes of acute bacterial cystitis within six months or three episodes within one year, with the latest UTI within the last 6 months)

(2) BMI between 18.5 and 32.0 kg/m$^2$ (3) Written informed consent to participate in the study Main Criteria for Exclusion:

(1) Acute urinary infection (2) Use of other vaginal applications, washes or sanitary products (3) Use of antibiotics in the last 4 weeks (4) Smoking (5) Use of probiotics (6) Not willing to abstain from sexual intercourse during the study (7) Relevant history or presence of any severe medical disorder, potentially interfering with this study in the investigator's judgement Further in- and exclusion criteria will be defined in the study protocol.

Pre-selection: based on qPCR analysis of gram-negative bacteria in relation to total bacteria, 30 subjects with the highest amounts of gram-negative bacteria will be selected from the 45 subjects.

26

Outcome Measures/Methodology:

Vaginal microbiota (16S rRNA analysis)

distribution of bacterial taxa at the phylum, family and genus level shifts of specific bacterial taxa Urine microbiota (16S rRNA analysis)

Distribution of bacterial taxa at the phylum, family and genus level shifts of specific bacterial taxa correlation of bacterial taxa between vaginal microbiota and urinary tract microbiota, if applicable qPCR analysis for gram-negative bacteria in relation to total bacteria (vaginal microbiota and urine microbiota)

pH value (twice a week)

Urinalysis (dip stick) on a weekly basis

Global Assessment

Questionnaire

Additional/Safety Parameters:

Tolerability

Adverse Events

Statistical Methods:

Descriptive statistics; Investigation of changes over time between baseline and end of intervention. Statistical methodology will be further described in the study protocol.

| Time | Screening phase inclusive pre-selection for gram negative bacteria appr. 3-4 weeks prior to start of run-in phase | Run-in phase 7 days | Visit 1 day 6 | Intervention phase 21 days | Visit 2 day 29 | Follow up phase 14 days | Visit 3 day 43 |
|---|---|---|---|---|---|---|---|
| Informed consent | x | | | | | | |
| Medical history and anamnesis including use of concomitant medication | x | | | | | | |
| Check of in- and exclusion criteria | x | | x | | | | |
| Hand in of vaginal swab (self-collection) for pre-Screening with qPCR | | x | | | | | |
| Hand out of study material (dip stick, devices for phi-meassurement, vaginal swabs, urine pots etc.) | | x | x | | x | | |
| Documentation of adverse events | | x | x | x | x | x | x |
| Questionnaire on vaginal symptoms | x | | x | | x | | x |
| Hand out of study cream | | | x | | | | |
| Application of cosmetic cream | | | x | x | | | |
| Vaginal pH-value | | x (e.g. twice a week) | | x (e.g. twice a week) | | x (e.g. twice a week) | |
| Sampling of vaginal swab (self-collection) for 16S rRNA analysis and qPCR analysis | | | x | | x | | x |
| Sampling of morning urine (self-collection) for 16S rRNA analysis and qPCR | | | x | | x | | x |
| Urine sample for urinalysis with dip stick | | x (on a weekly basis) | x | x (on a weekly basis) | x | x (on a weekly basis) | x |
| Compliance | | | | | x | | |
| Tolerability | | | | | x | | |
| Global assessment | | | | | x | | |

Example 9

Study Design to Evaluate the Impact of a Bdello Topical Cream on HVE Models

An HVE model will be colonized with *Lactobacillus* sp. in order to assess the biological efficacy of Bdello in a cream-formulation on bacterial viability, growth, adhesion to vaginal epithelium. In a second step the Bdello cream will be assessed for its competitive efficacy in counteracting *E. coli* epithelial adhesion, toxicity and proliferative capacity.

Experimental Designs

Test system: SkinEthic Reconstructed Human Vaginal Epithelium (HVE) of 0.5 cm$^2$ at day 12 of differentiation.

Part 1: HVE Colonized with *Lactobacillus* sp.

HVE will be colonized with $10^6$ *Lactobacillus* sp. inoculum according to internal procedure:

The study will be conducted on triplicate HVEs on the following series:

HVE negative control

HVE colonized

HVE colonized and treated with placebo (cream without active)

HVE colonized and treated with test item at the following treatment times

HVE colonized with 2-3 lactobacilli strains during 24H: to assess efficacy in protecting the resident ecoflora: no negative effect on the viability and adherence of *Lactobacillus* spp.

Testing parameters: Viable count on apical and homogenate, SEM analysis (separate series)

Optional: Lactic acid production, GRAM staining to show a different bacilli distribution on epithelium surface.

Part 2: HVE Model: Competition with *E coli*: Anti Microbial Adhesion

*E. coli* is uropathogenic microorganism that can derive from the gut and infect the urogenital tract. *E. coli* modify epithelial cells via adherence, invasion and barrier impairment. In turn epithelial cells respond to pathogen infection by secreting proinflammatory cytokines (IL-1α and TNF-α) and anti-microbial peptides that inhibit the microorganism growth.

Testing series on triplicate tissues.

Negative control: HVE COLONIZED with Lactobacilli

Positive controls:

1. HVE COLONIZED with Lactobacilli and then infected with *E. coli*

2. HVE infected with *E. coli.*

Preventive efficacy: a pre-treatment with the cream in presence of lactobacilli will be performed according to the product mode of use (to be defined) and this will be followed by inoculum of *E. coli* for 4 h according to internal procedure.

Treatment on established competition model: Lactobacilli+*E. coli* during 4 h

Read out parameters quantified at the end of the infection with *E. coli* (4 h):

Viable count, SEM analysis, release of IL-1α, HVEs (simplicate) will be fixed in buffered formalin for further HIC analysis (barrier differentiation-involucrin, boosting antimicrobial defense-βDEF2).

Part 3: Mildness on HVE

The mildness and soothing properties can be assessed on standard HVE model (not Colonized) where an inflammatory status is induced by an irritant (sodium dodecyl phosphate) during a short period time: on the inflamed HVE the cream is applied during 24 h and the release of IL-1α in the culture media in all series is performed.

Testing series on triplicate tissues:

Negative control: without irritation stimulus

Positive control: Inflamed HVE

Sample: Inflamed HVE+cream (active ingredient)

The HVE at the end of the exposure can be used for histomorphological investigation to confirm the beneficial effect of the cream.

The invention claimed is:

1. A method of maintaining or re-establishing a subject's healthy genital microbiome, the method comprising administering a predatory bacterium to the external genital area of the subject and/or the vagina of the subject, wherein the predatory bacterium is *Bdellovibrio bacteriovorus.*

2. The method of claim 1, wherein the genital microbiome is a vaginal microbiome.

3. The method of claim 2, wherein the healthy vaginal microbiome comprises more than 80% *Lactobacillus* species and/or more than 5% *Bifidobacterium* species.

4. A method of prophylaxis or treatment of a gram-negative bacterial infection in a subject in need thereof, the method comprising administering a predatory bacterium to the external genital area of the subject and/or the vagina of the subject, wherein the predatory bacterium is *Bdellovibrio bacteriovorus.*

5. The method of claim 4, wherein the bacterial infection is caused by a species of one or more of the following pathogenic bacteria genera:

*Escherichia, Klebsiella, Gardnerella, Prevotella, Bacteroides, Mobiluncus, Salmonella, Proteus, Pseudomonas, Chlamydia* and *Neisseria.*

6. The method of claim 2, wherein the healthy vaginal microbiome comprises more *Lactobacillus* species than other bacterial species.

\* \* \* \* \*